US00PP21355P2

(12) United States Plant Patent
Meilland

(10) Patent No.: US PP21,355 P2
(45) Date of Patent: Oct. 5, 2010

(54) GRANDIFLORA ROSE PLANT NAMED 'MEIKARADY'

(50) Latin Name: *Rosa hybrida*
Varietal Denomination: Meikarady

(75) Inventor: Alain A. Meilland, Le Luc (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/453,591

(22) Filed: May 15, 2009

(51) Int. Cl.
*A01H 5/00* (2006.01)

(52) U.S. Cl. ..... Plt./132
(58) Field of Classification Search ..... Plt./132
See application file for complete search history.

*Primary Examiner*—Kent L Bell
(74) *Attorney, Agent, or Firm*—Buchanan Ingersoll & Rooney PC

(57) ABSTRACT

A new and distinct variety of Grandiflora rose plant is provided that forms in abundance on a substantially continuous basis attractive double blossoms that are red-purple margined with red in coloration and display a pleasant fragrance. The vegetation is strong and a semi-erect growth habit is displayed. No particular susceptibility to disease has been noted during observations to date. The plant is particularly well suited for providing distinctive attractive ornamentation in the landscape.

1 Drawing Sheet

Figures 1, 2, 3, 4, 5, 6, 7, 8, 9, 10, 11, 12, 13, 14, 15, 16:
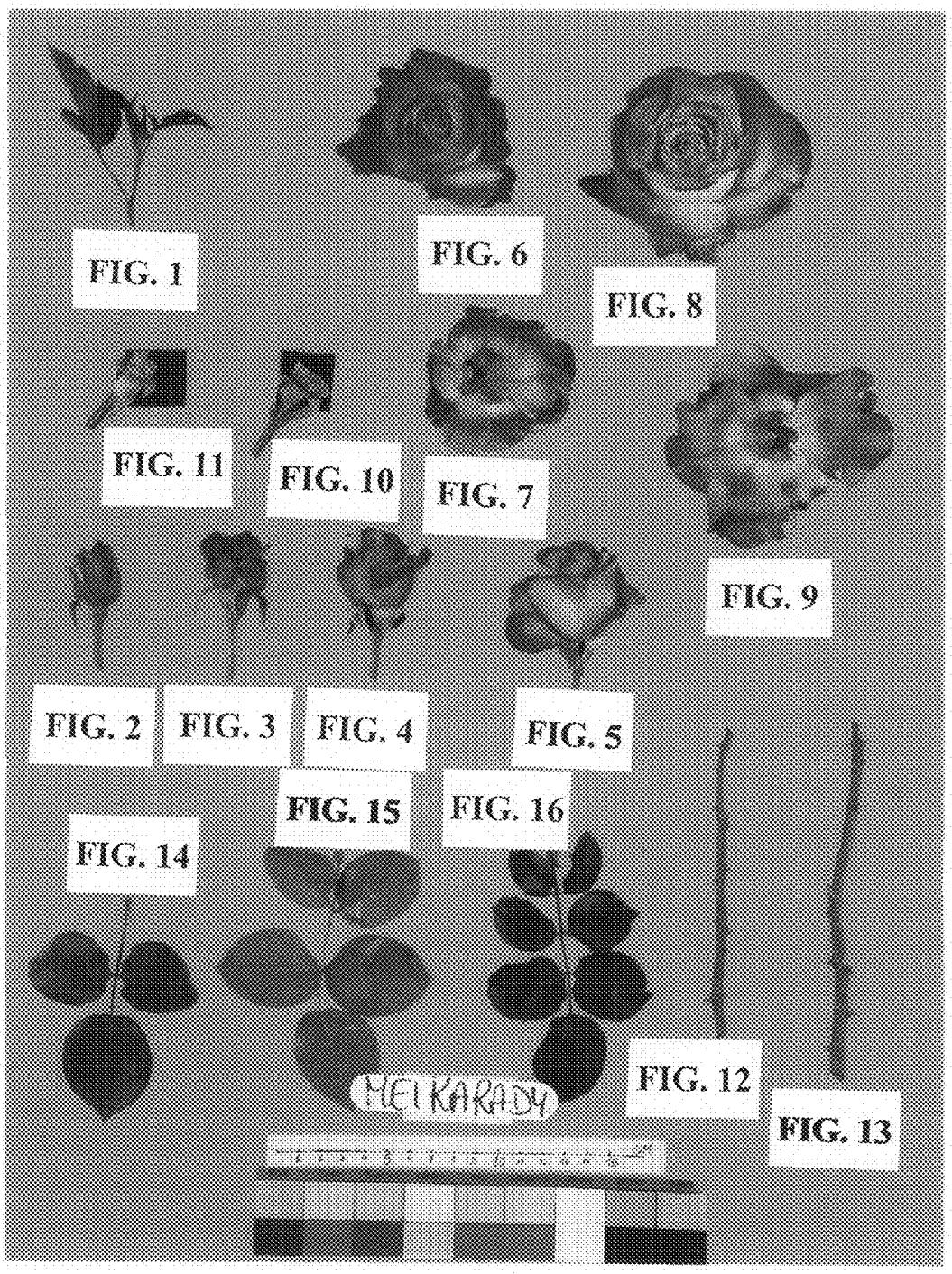

Botanical/commercial classification: *Rosa hybrida*/Grandiflora Rose Plant.

Varietal denomination: cv. Meikarady.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the product of the cross of the 'Meigriso' variety (non-patented in the United States) and the 'Jacpico' variety (U.S. Plant Pat. No. 3,997). The male parent (i.e., the pollen parent) was the 'Twobe' variety (U.S. Plant Pat. No. 7,901). The parentage of the new variety can be summarized as follows:

('Meigriso'×'Jacpico')×'Twobe'.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms strong vegetation,
(b) displays a semi-erect growth habit,
(c) abundantly and substantially continuously forms attractive large double blossoms that are red-purple margined with red in coloration and display a pleasant fragrance,
(d) displays attractive semi-glossy dark green foliage, and
(e) is particularly well suited for providing distinctive attractive ornamentation in the landscape.

The new variety well meets the needs of the horticultural industry and can be grown to advantage in parks and gardens.

The new variety can be readily distinguished from its ancestors upon an examination of the blossoms. For instance, 'Meigriso' variety is a Hybrid Tea that forms ruby red blossoms with a white reverse. The 'Jacpico' variety is a Hybrid Tea which forms white blossoms with a pink blush. The 'Twobe' variety is a Hybrid Tea which forms soft creamy pink blossoms with darker pink edges.

The new variety has been found to undergo asexual propagation at the south of France by a number of routes, including budding, grafting, and the use of cuttings. Such asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meikarady'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during October while budded on *Rosa froebelli* understock and growing outdoors at Le Cannet des Maures, Var, France. Dimensions in centimeters are indicated at the bottom of the photograph together with comparative color information.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface; and FIG. 16 — illustrates a specimen of a leaf with seven leaflets — plan view — upper surface.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of one-year-old plants during October while growing outdoors on *Rosa froebeffi* understock at Le Cannet des Maures, Var, France.

Class: Grandiflora.

Plant:

*Habit.*—Semi-erect.

*Height.*—Approximately 70 cm on average.

*Width.*—Approximately 40 cm on average.

Branches:

*Young shoots.*—Commonly approximately 18 cm in length on average, and approximately 0.3 cm in diameter on average.

*Adult branches.*—Commonly approximately 50 cm in length on average, and approximately 0.7 cm in diameter on average.

*Color.*—Young shoots: near Yellow-Green Group 144A and lightly suffused with Greyed-Purple Group 184B. Adult wood: near Yellow-Green Group 146B.

*Thorns.*—On young stems: Small prickles: Configuration: upright and longish pointed on the upper surface and slightly concave on the under surface with a narrow and long base. Quantity: approximately 7 on average on a stem length of 10 cm. Length: approximately 0.3 cm on average. Color: near Greyed-Orange Group 165B. Long prickles: Configuration: upright and longish pointed on the upper surface and slightly concave on the under surface with a narrow and long base. Quantity: approximately 8 on average on a stem length of 10 cm. Length: approximately 0.8 cm on average. Color: near Greyed-Orange Group 163B. On adult stems: Small prickles: Configuration: upright and longish pointed on the upper surface and slightly concave on the under surface with a narrow and long base. Quantity: approximately 15 on average on a stem length of 18 cm. Length: approximately 0.3 cm on average. Color: near Greyed-Orange Group 165B. Long prickles: Configuration: upright and longish pointed on the upper surface and slightly concave on the under surface with a narrow and long base. Quantity: approximately 11 on average on a stem length of 18 cm. Length: approximately 0.7 cm on average. Color: near Greyed-Orange Group 165C.

Leaves:

*Stipules.*—Adnate, pectinate, and broad, approximately 2 cm in length on average, approximately 1 cm in width on average, near Green Group 139B on the upper surface, and near Green Group 138B on the under surface.

*Petioles.*—Upper surface: near Yellow-Green Group 146A in coloration. Under surface: near Yellow-Green Group 147C in coloration. Texture: slightly glandular and commonly bear very few prickles on both surfaces. Length: approximately 3.9 cm for the terminal leaflet.

*Rachis.*—Upper surface: near Yellow-Green Group 146B in coloration. Under surface: near Yellow-Green Group 146C in coloration. Texture: commonly bear some prickles.

*Leaflets.*—Number: 3, 5 (most often), and 7. Shape: generally oval with a rounded base and a somewhat rounded tip. Size: the terminal leaflets commonly are approximately 6.5 cm in length on average, and approximately 4.2 cm in width on average. Serration: small and single (as illustrated). Texture: semi-glossy on the upper surface. General appearance: rather dense. Color (young foliage): Upper surface: near Green Group 141A. Under surface: near Yellow-Green Group 146B and slightly suffused with Greyed-Red Group 181A. Color (adult foliage): Upper surface: near Green Group 135A. Under surface: near Yellow-Green Group 147B.

Inflorescence:

*Number of flowers.*—Pluriflorous, commonly one flower per stem.

*Peduncle.*—Pubescent, near Yellow-Green Group 146C in coloration, approximately 7 cm in length on average, and approximately 0.5 cm in diameter on average.

*Sepals.*—Upper surface: tomentose and near Green Group 137D in coloration. Under surface: smooth and near Yellow-Green Group 146B in coloration. Configuration: approximately 2.8 cm in length on average, approximately 1 cm in width on average at the widest point, and longish-pointed at the tip and narrow with an upright base.

*Buds.*—Shape: globular. Size: medium. Length: approximately 3.7 cm on average. width: approximately 3.5 cm on average at the widest point. Color: Upper surface: near Red-Purple Group 62D amply suffused with near Red-Purple Group 62B, and margined with Red-Purple Group 63A. Under surface: near Red-Purple Group 63C amply suffused with near Red-Purple Group 63A and 63B.

*Flower.*—Shape: cup-shaped. Diameter: approximately 9 cm on average. Color (in the course of opening): Upper surface: near Red-Purple Group 65D amply suffused with Red-Purple Group 65B and near Red-Purple Group 68B. Under surface: near Red-Purple Group 62D very amply suffused with Red-Purple Group 63A, 63B, and 63C. Color (when fully open): Upper surface: near Red-Purple Group 56B very amply suffused with near Red-Purple Group 62B and margined with near Red-Purple Group 61C. Undersurface: near Red-Purple Group 62C suffused with near Red-Purple Group 62B and amply margined with Red-Purple Group 63A. Fragrance: displays a pleasant fragrance of medium strength. Petal number:

commonly approximately 38 on average under normal growing conditions. Petal shape: generally with a rounded tip and a rounded base. Petal size: commonly approximately 5 cm in length on average, and approximately 5 cm in width on average. Petal texture: relatively thick. Petal margins: soft and somewhat ruffled. Petal arrangement: imbricated, and without petaloids. Petal drop: good with the petals commonly detaching cleanly before drying. Stamen number: approximately 198 on average. Anthers: regularly arranged around the styles, approximately 0.2 cm in length on average, approximately 0.1 cm in width on average, and near Yellow Group 12B in coloration. Pollen: present. Filaments: approximately 0.7 cm in length on average, and near Red Group 46B in coloration. Pistils: approximately 162 on average. Stigmas: approximately 0.2 cm in length on average, approximately 0.05 to 0.1 cm in width on average, and near Red Group 46C in coloration. Styles: approximately 0.6 cm in length on average, and near Yellow Group 2C in coloration. Receptacle: smooth, funnel-shaped in longitudinal section, approximately 1.2 cm in length on average, approximately 1.3 cm in width on average at the widest point, and near Green Group 137D in coloration. Lastingness: commonly approximately 10 to 12 days on average on the plant, depending upon environmental conditions, and approximately 8 days on average when cut and placed in a vase.

Development:

*Vegetation.*—Strong and vigorous.

*Blooming.*—Early season, abundant and substantially continuous.

*Resistance to diseases.*—Good, with no particular disease susceptibility having been noted during observations to date.

I claim:

1. A new and distinct Grandiflora rose plant characterized by the following combination of characteristics:

(a) forms strong vegetation, (b) displays a semi-erect growth habit, (c) abundantly and substantially continuously forms attractive large double blossoms that are red-purple margined with red in coloration and display a pleasant fragrance, (d) displays attractive semi-glossy dark green foliage, and (e) is particularly well suited for providing distinctive attractive ornamentation in the landscape;

substantially as herein shown and described.

* * * * *

HEIKARADY